United States Patent [19]
Kingsley et al.

[11] Patent Number: 5,371,283
[45] Date of Patent: Dec. 6, 1994

[54] TEREPHTHALIC ACID PRODUCTION

[75] Inventors: Jeffrey P. Kingsley, Newburgh; Anne K. Roby, Peekskill; Lawrence M. Litz, Pleasantville, all of N.Y.

[73] Assignee: Praxair Technology, Inc., Danbury, Conn.

[21] Appl. No.: 168,497

[22] Filed: Dec. 22, 1993

[51] Int. Cl.⁵ .............................................. C07C 51/16
[52] U.S. Cl. ..................................................... 562/416
[58] Field of Search ......................................... 562/416

[56] References Cited

U.S. PATENT DOCUMENTS

| | | | |
|---|---|---|---|
| 4,243,636 | 1/1981 | Shiraki | 562/416 |
| 4,827,025 | 5/1989 | Shiraki | 562/416 |
| 4,900,480 | 2/1990 | Litz et al. | 261/36.1 |
| 5,068,406 | 11/1991 | Holzhauer | 562/416 |

*Primary Examiner*—Michael L. Shippen
*Attorney, Agent, or Firm*—Alvin H. Fritschler

[57] ABSTRACT

Oxygen or an oxygen-rich gas is used in the production of terephthalic acid in a reaction system that mitigates the flammability hazards associated therewith. Lower reactant and solvent consumption is achieved, with lower production of unwanted by-products, lower gas handling costs and lower environmental impact concerns than with conventional air based terephthalic acid production.

20 Claims, 2 Drawing Sheets

TEREPHTHALIC ACID PRODUCTION

BACKGROUND OF THE INVENTION

1. Field of the Invention

This invention relates to the production of terephthalic acid. More particularly, it relates to an enhanced process for the production of said terephthalic acid.

2. Description of the Prior Art

In a typical air or enriched air based process for producing terephthalic acid, liquid p-xylene is fed to a stirred tank reactor, with a monobasic aliphatic acid, typically acetic acid being used as a solvent. The ratio of solvent to reactant is typically one to ten weights of solvent per volume of reactant (1:1 to 10:1). The reaction is catalyzed with a heavy metal or mixture of heavy metals, most commonly cobalt and manganese in the form of acetate salts. In addition, bromine, in the form of bromic acid, is commonly used as an initiator. The reactor is maintained at an operating temperature of between 170° C. and 225° C. The operating pressure is generally between 100 and 300 psig. Compressed air or enriched air, typically having between 21% and 28% oxygen, is sparged into the bottom of the reactor. Oxygen from the air is dissolved into the liquid phase and reacts with the p-xylene to produce the desired terephthalic product. Intermediate oxidation products and by-products are also formed in quantities that depend on the reaction conditions employed. At a residence time of one hour, the conversion of p-xylene is typically about 99%, with the yield to desired terephthatic product being greater than 96%.

The most important intermediate oxidation product in the production of terephthalic acid (TPA) is 4-carboxybenzaldehyde (4CBA), which is one oxidation step removed from terephthalic acid. The presence of 4CBA in the TPA product is undesirable. It acts as a chain terminator in subsequent polymerization reactions which convert TPA to its most important end products, i.e., polyester fibers and polyethylene terephthalate resins. For a given residence time, the conversion of 4CBA to TPA has been observed to increase with temperature. Hence, the concentration of 4CBA in the TPA product decreases with increased operating temperature, so that TPA product quality increases at higher operating temperatures.

Raw material losses to undesirable by-products, on the other hand, also increase with temperature. The acidic acid solvent and, to a lesser extent, p-xylene, react to produce carbon dioxide, carbon monoxide, methyl bromide and methyl acetate, all of which are environmentally sensitive materials. Since a high reaction temperature must be maintained to make product terephthalic acid that meets applicable quality standards, the loss of acetic acid and the commensurate production of byproduct gases is usually a significant factor in the economics of the overall operation.

In such known operations, feed air must be compressed to a pressure somewhat above the reactor operating pressure before it is blown into the reactor through a pipe or other submerged sparger. As the air bubbles are dispersed in the reactor and are circulated through the body of liquid reactant and solvent by an agitator device, the oxygen concentration in the air bubbles decreases as the oxygen dissolves and reacts with the TPA. The residual air bubbles disengage from the liquid phase and collect in a gas space at the top of the reactor to form a continuous gas phase. This waste gas must be vented in order to provide space for fresh air feed, while maintaining adequate gas hold-up in the reactor to promote the desired oxygen transfer from the air to the liquid phase.

To avoid the possibility of fire or explosion, the oxygen concentration in the gas space at the top of the reactor must be maintained below the flammable limit. For practical operating purposes, the oxygen concentration must be maintained at less than 8–9% by volume. More typically, the oxygen concentration in the gas space is maintained below 5% by volume to provide a safe margin below the flammable limit. Thus, in a well stirred tank reactor, the average concentration of oxygen in the circulating air bubbles must be below 5% in order to insure that the average concentration of oxygen in the gas that collects in the headspace of the reactor is nonflammable.

The oxygen concentration in the gas space is a function of the rate at which air or enriched air is fed into the reactor and the rate of consumption of oxygen from the air by reaction with p-xylene. The rate of reaction and, therefore, the TPA production rate per unit of reactor volume, increases with temperature, pressure, oxygen concentration in the gas phase, p-xylene concentration, promoter concentration and catalyst concentration. Since the concentration of dissolved oxygen in the liquid phase and, hence, the reaction rate of oxygen, is proportional to the oxygen concentration in the gas phase, for a given set of reaction conditions, the 5% oxygen restriction in the headspace effectively limits the oxygen reaction rate.

As air bubbles circulate within the reactor, acetic acid, water, volatile organic chemicals (VOC's) and byproduct gases such as $CO_2$, CO, methyl bromide and methyl acetate evaporate into the bubbles and collect in the continuous gas phase which is vented from the reactor. The total amount of volatile species which leave the reactor with the vent gas is proportional to total gas throughput, which is proportional to the air feed rate. The amount of byproduct gases which leave the reactor with the vent gas depends on their rate of formation.

The federal, state and local air quality standards which apply to a particular production facility determine the degree to which these species must be removed from the vent gas before it is released to the atmosphere. Acetic acid is a valuable solvent in the process so it is usually condensed and recycled to the reactor. Residual organic compounds are usually stripped from the vent gas which produces a liquid waste stream from the stripper bottoms. Some vent gas treatment systems may also include $CO_x$ and methyl bromide abatement systems to meet air quality standards. Since the total amount of material which must be removed from the vent gas is proportional to the air feed rate, the size of the vent gas treatment equipment and the amount of waste which is generated in the process is similarly proportional to the air feed rate.

Clearly, air or said enriched air, typically 21% to 28% oxygen, based TPA plant design requires optimization of temperature, pressure, catalyst loading, air feed rate, reactor volume, and vent gas treatment equipment. For example, increasing temperature increases productivity per unit reactor volume and improves product purity, but it also leads to yield and solvent losses, and byproduct gas formation due to over oxidation.

In the air based terephthalic acid production process as described above, a relatively high operating temperature is required in order to complete the oxidation of 4CBA to TPA, and thereby produce said TPA that meets applicable product quality standards. The high temperature required for product purity also results in significant reaction of acetic acid, and to a lesser extent of product p-xylene, to unwanted by-products, such as $CO_2$, CO, methyl bromide and methyl acetate, is noted above. As those skilled in the art will appreciate, there is a significant operating cost penalty associated with providing makeup acetic acid to the process, and with loss of p-xylene reactant and the related disposal of waste material. There is also a significant environmental impact associated with the formation of $CO_x$, methyl bromide, methyl acetate and other emissions.

In addition, in the air based process, there is a substantial capital and operating cost penalty associated with the compression of the nitrogen in the feed air stream. The nitrogen is inert and does not contribute to the efficiency of the reaction process. In addition, there is a significant capital and operating cost penalty associated with treating the vent gas. These costs are proportioned to the amount of nitrogen that is introduced into the reactor vessel in the air feed thereto.

It is an object of the invention, therefore, to provide an improved process for the production of terephthalic acid.

It is another object of the invention to provide a terephthalic acid production process reducing the amount of byproduct and waste gas generation.

With those and other objects in mind, the invention is hereinafter described in detail, the novel features thereof being particularly pointed out in the appended claims.

SUMMARY OF THE INVENTION

The reaction to produce terephthalic acid is carried out using oxygen in place of the air feed, and employs a reactor system that mitigates the flammability hazards associated with this substitution. Terephthalic acid of equivalent quality to that of the conventional air-based process is produced, but with lower consumption of acetic acid and of p-xylene and with lower production of unwanted by-products, lower gas handling costs and lower environmental impact concerns.

BRIEF DESCRIPTION OF THE DRAWINGS

The invention is hereinafter further described with reference to the accompanying drawings in which.

DETAILED DESCRIPTION OF THE INVENTION

The objects of the invention are accomplished by carrying out the desired terephthalic acid production using oxygen instead of air, in a reactor adapted to obviate the potential for fire or explosion, under unique TPA operating conditions serving to minimize the amount of undesired by-products present in the terephthalic acid product and the amount of vent gases to be treated. The invention is thus carried out at lower operating temperatures and pressure than are used in the conventional air based process, while achieving equivalent TPA production. Furthermore, the undesired reactions that consume solvent and reactant, and produce by-product gases, are suppressed at the lower operating temperature conditions of the invention.

In the process of the invention, a so-called Liquid Oxidation Reactor (LOR) system is conventionally employed to ensure that oxygen and the body of liquid are advantageously mixed and recirculated without appreciable loss of oxygen to the overhead gas phase. The LOR system is described in the Litz et al. patent, U.S. Pat. No. 4,900,480. A convenient embodiment thereof is that of FIG. 2 of said Litz patent.

Figure 1:
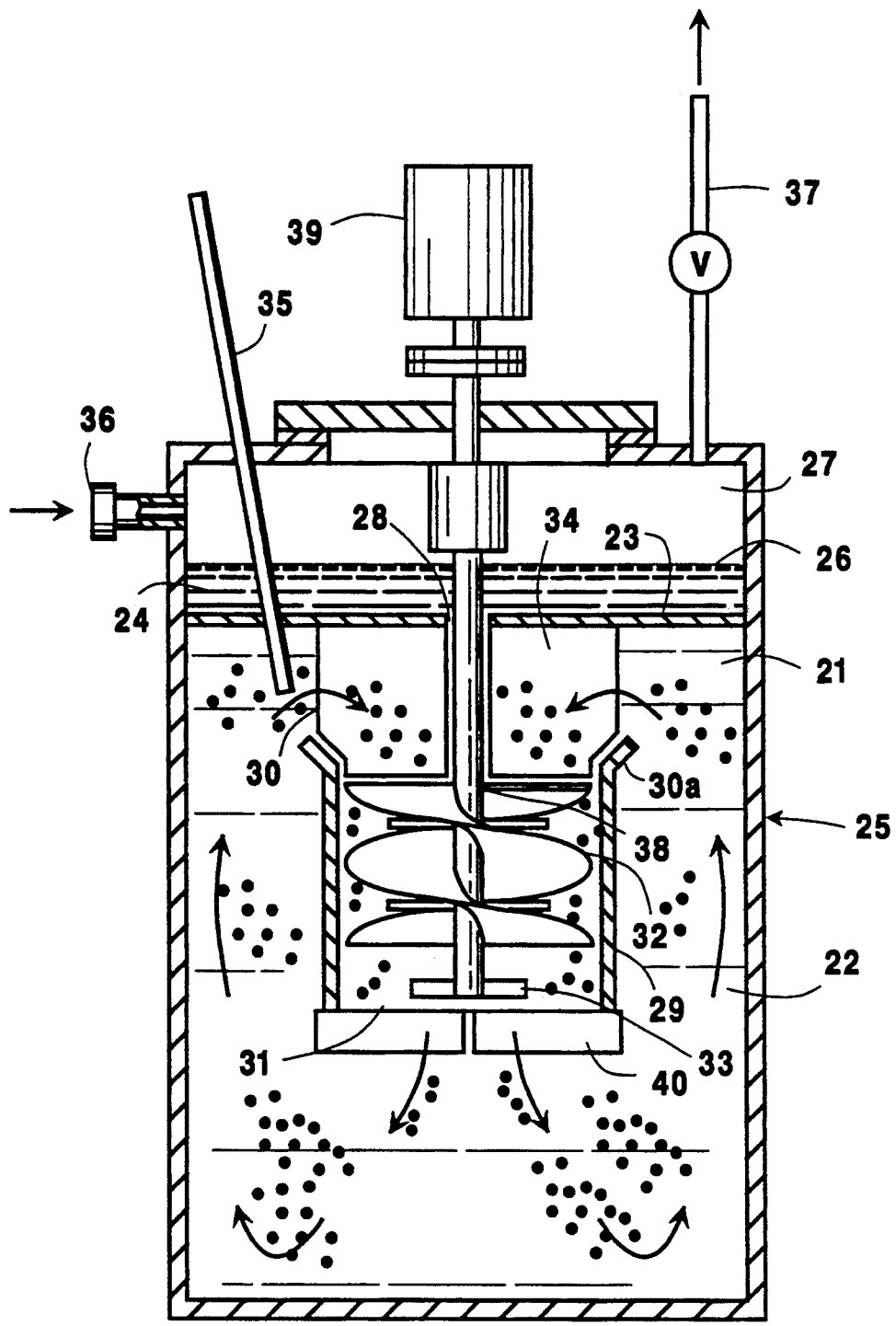
FIG. 1 is a schematic side elevational view of an embodiment of the reactor vessel employed in the practice of the invention.

FIG. 1 of the drawings hereof describes said convenient embodiment of the LOR System as used in the practice of the invention. In this embodiment, the major portion 22 of liquid body 21 is separated by baffle means 23 from quiescent portion of liquid 24 in reactor vessel 25. Said quiescent portion 24 has a gas-liquid interface 26 with overhead gas phase 27. Opening 28 in said baffle means 23 establish fluid communication between major portion 22 and quiescent portion 24 of said liquid body 21. Major portion 22 is maintained in recirculating flow conditions by the essentially central positioning within reactor vessel 25 of a hollow draft chamber 29 such that the open ends thereof, i.e., ends 30 and 31 are at the top and bottom thereof, respectively, and impeller means 32 are positioned within said hollow draft chamber 29. Such impeller means 32 are typically helical impeller means adapted to facilitate the downward flow of the oxygen bubble-liquid mixture in the draft chamber and upward flow outside said chamber. Impeller means 32 may, if desired, include radial flow impeller means 33 and lower baffle means 40, similar to the guide baffle means referred to below, to reduce the size of the oxygen bubbles that are maintained in the indicated recirculating flow conditions as the oxygen bubble-liquid mixture in major portion 22 of liquid body 21 is caused to pass downward through hollow draft chamber 29 and up to the outer sides of hollow draft chamber 29. The flow of said oxygen bubble-liquid mixture into the top end 30 and out of the bottom end 31 of said hollow draft chamber 29 is desirably facilitated by the directing of said mixture to top inlet end 30 by guide baffle means 34 positioned at the upper portion of said major portion 22 of liquid body 21 below baffle means 23. Said baffle means 23 are desirably positioned so as to obviate the accumulation of individual oxygen bubbles thereunder.

The feed oxygen stream is injected directly into major portion 22 of liquid body 21 through conduit means 35 so that the bubbles of oxygen formed in the liquid are readily maintained essentially in dispersed form in the recirculating liquid in said major portion of the body of liquid. Gas inlet means 36 and outlet vent means 37 are provided to enable nitrogen or other inert gas to be passed, if desired, through overhead gas phase 27 to assure that the concentration of oxygen or other inflammable gas is maintained below its flammability limit. Impeller means 32 include a suitable drive shaft 38 that extends upward through opening 28 in baffle means 23 for connection with suitable driving means generally represented by the numeral 39. It will be noted that hollow draft chamber 29, in particular applications, desirably includes a conically flared portion 30a at the upper end thereof, to further facilitate the flow of the oxygen bubble-liquid mixture into said draft chamber of downward passage therein.

The LOR system, as described above and variations thereof, enables pure oxygen to be safely employed in place of air for terephthalic acid production. The conventional air sparger system as used in the prior air based terephthalic acid production process is not suitable and would be generally inefficient if used with oxygen instead of air. In the oxygen based process of the invention, the amount of nitrogen that is introduced into the process, and, therefore, the amount of vent gas that must be treated, is reduced by a factor of about 24 compared to the air based process. Thus, the capital and operating expenses associated with feed gas compression and vent gas treating are greatly reduced compared to the air based process.

In the operation of the oxygen based process of the invention in the LOR system, oxygen is fed under the baffle that separates the recirculating liquid phase from the quiescent portion of the body of liquid and the vent space of the reactor, such that it is drawn, with the recirculating liquid, down through the impeller and dispersed throughout the recirculating liquid phase. The horizontal baffle allows some of gas leakage to prevent the build-up of waste gases in the reaction zone. A purge stream of nitrogen or other inert gas is blown across the liquid surface of the quiescent zone to reduce the oxygen concentration in the headspace. The flow rate of the purge stream is adjusted such that the concentration of oxygen in the headspace is maintained below the explosive limit. For the illustrated system and generally in the practice of the invention, the oxygen concentration in the vent is suitably maintained below 7.5%, typically below 5%.

In the TPA production operation, a significant amount of organic material and water evaporate from the reaction mixture. The vent gases are desirably cooled, and the condensibles therefrom are returned to the reactor in preferred embodiments of the invention. A portion of the vent flow is desirably diverted for gas analysis of carbon dioxides and oxygen. The oxygen utilization efficiency observed in the practice of the invention for the reaction of p-xylene with oxygen is greater than 99%. That is, less than 1% of the oxygen that is fed to the reactor is vented unreacted.

The relative benefits due to the use of oxygen in accordance with the practice of the invention instead of air in the conventional process for the production of TPA are observed over the range of suitable operating conditions, and the optimal operating conditions for the oxygen-based process of the invention are generally more favorable than those that pertain in the practice of the conventional air based process.

The solvent: reactant ratio is from about 1:1 to about 8:1 on a wt/volume basis in the practice of the invention. The catalyst for the desired oxidation reaction is a mixture of cobalt and manganese, preferably as acetate salts. The catalyst loading should be between 500 and 3,000 ppm, with the ratio of cobalt to manganese being from 0.1 to 10:1, preferably about 3:1 on a weight basis. Bromine is used as an initiator and is added conveniently as hydrogen bromide (HBr). The bromine loading is between 0.1:1 and 1:1 on a weight basis relative to the total catalyst loading, preferably about 0.3:1. The residence time for the liquid is between 30 and 90 minutes. The operating temperature is generally between 150° C. and 200° C. The operating pressure is between 100 psig and 200 psig.

Figure 2:
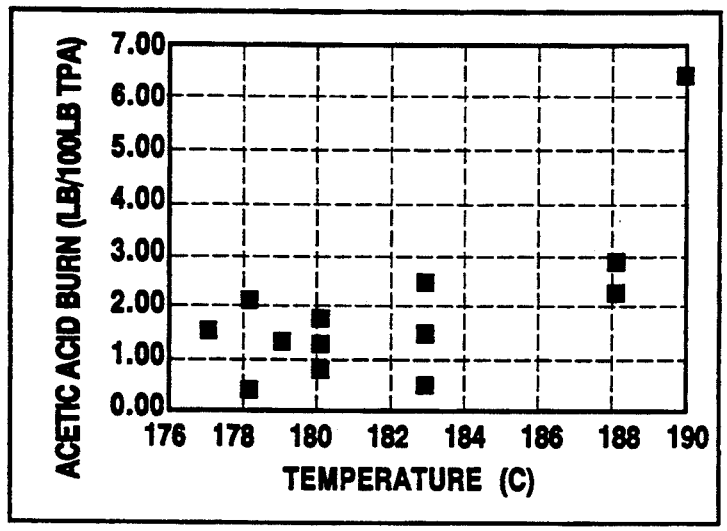
FIG. 2 is a plot showing the affect of operating temperature on acetic acid burn.
Figure 3:
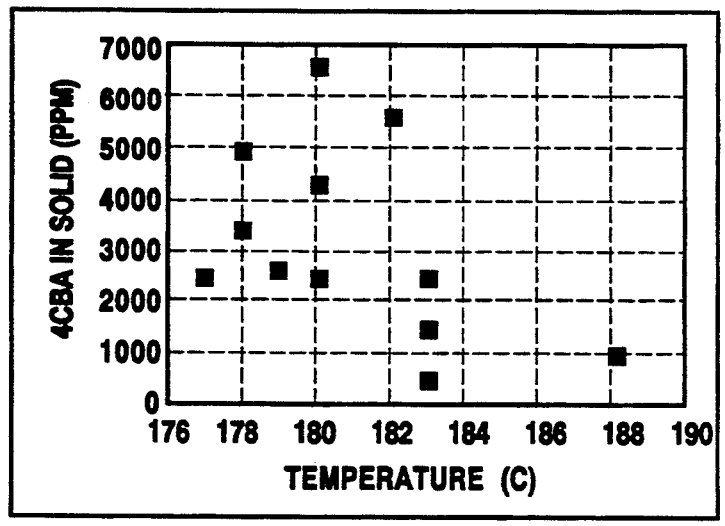
FIG. 3 is a plot showing the affect of operating temperature on the concentration of 4-carboxybenzaldehyde (4CBA) in the terephthalic acid product.

It should be noted that the optimal operating conditions for a specific embodiment of the invention are largely determined by the economics applicable to that embodiment. As indicated above, an increase in operating temperature increases solvent loss and improves product quality. This affect of temperature on these two parameters can be seen from the data presented in FIGS. 2 and 3 of the drawing. FIG. 2 shows the affect of operating temperature on acetic acid burn. FIG. 3 shows the affect of operating temperature on the concentration of 4CBA in the product. As noted above, as the level of 4CBA increases, product quality decreases. Based on the data shown in FIGS. 2 and 3, the preferred operating temperature for the practice of the invention has been found to be about 180° C., with the preferred operating pressure being between 130 psig and 150 psig. Thus, desirably milder operating conditions can be employed in the practice of the invention than are generally employed in the practice of the conventional air based process for terephthalic acid production.

In the practice of an illustrative embodiment of the invention using the reactor system shown in FIG. 1, the relative flow rates for major components of the subject oxidation reaction are as follows with the flows being based on 100 lb. liquid feed. The liquid feed introduced to the reactor comprises 20 lb. p-xylene, 70 lb. acetic acid, 10 lb. water, 0.22 lb. cobalt acetate, 0.08 lb. manganese acetate and 0.02 lb. hydrobromic acid. An oxygen feed of 18.5 lb. provides a liquid product stream of 69 lb. acetic acid, 30.5 lb. terephthalic acid, 17.5 lb. water, 0.22 lb. cobalt acetate, 0.08 lb. manganese acetate, 0.02 lb. hydrobromic acid and 0.08 lb. xylene. A 2 lb. nitrogen purge gas is used, with the vent gas being 2 lb. nitrogen, 1.20 lb. carbon dioxide, 0.60 lb. carbon monoxide and 0.23 lb. oxygen.

The undesired production of methyl acetate in the conventional air based TPA production process is reported to be approximately 0.4/100 lb. of TPA produced. In the oxygen based process as described and claimed herein, such methyl acetate production can be decreased very appreciably, with test data indicating that the methyl acetate production can be decreased to less than 0.2 lb./100 lb. of TPA production in particular embodiments of the invention. Production of carbon monoxide and carbon dioxide can likewise be cut by nearly an order of magnitude in the practice of the invention. A similar decrease in the undesired production of the environmentally sensitive by-product, methyl bromide, can likewise be expected in the practice of the invention.

Figure 4:
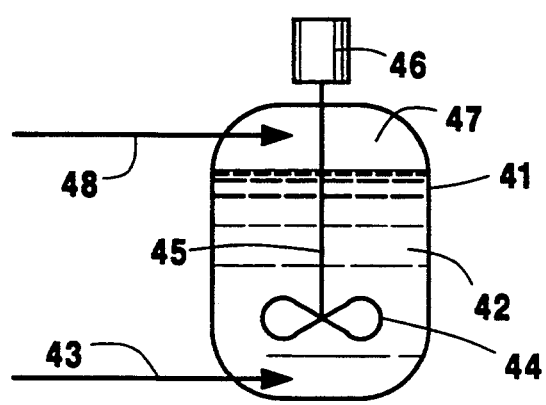
FIG. 4 is a schematic side elevational view of another embodiment of the invention.

While the reactor vessel illustrated in FIG. 1 and variations thereof are preferred, it will be understood that conventional reactor designs can also be used in processes in which oxygen is substituted for air in TPA production. Such a reactor system is illustrated in FIG. 4 of the drawings. As shown therein, reactor vessel 41 contains a body of liquid reactant 42, with oxygen being added thereto through line 43. Paddle agitator 44 or other suitable impeller means, is provided to facilitate dispersion of gas bubbles in the liquid. Drive shaft 45 extends upward and out of reactor vessel 41 for connection with suitable drive means 46. Nitrogen or other vent gas is introduced into overhead gas space 47 in said reactor vessel 41 through inlet line 48, with vent gases being withdrawn from reactor vessel 41 through outlet line 49.

Many of the advantages recited above for the preferred embodiments of the invention would be realized in the practice of the FIG. 4 embodiment, i.e., increased reaction rate, decreased vent flow, reduction in by-product formation. However, to avoid the safety problems associated with excess oxygen in the gas space of reactors such as that illustrated in FIG. 4, a large nitrogen flood to the overhead gas space must be provided. In addition, the oxygen utilization efficiency for such systems is much lower than for the LOR system embodiments of the invention because there is no provision for the recirculation of unreacted oxygen such as occurs in the enhanced recirculation of unreacted oxygen bubbles in the recirculating major portion of the body of liquid using the LOR system. Thus, more oxygen would be required, since more of the oxygen passed to the reactor would be vented unreacted. The additional amounts of oxygen and nitrogen required in the FIG. 4 approach, and the associated costs, render the FIG. 4 embodiment less desirable, and perhaps uneconomical, for various applications of the TPA production operation.

Those skilled in the art will appreciate that various changes and modifications can be made in the details of the invention without departing from the scope thereof as recited in the appended claims. For example, a solvent other than acetic acid, e.g., a monobasic aliphatic acid containing two to four carbon atoms, could be employed. While essentially pure oxygen is advantageously employed in the preferred embodiments of the invention, other oxygen-rich gas having a significantly higher oxygen content than air, i.e., oxygen-enriched air having at least about 50%, preferably at least about 90%, oxygen, can also be used in various embodiments of the invention.

The invention enables an important advance to be achieved in the commercially significant field of TPA production. By enabling by-product and waste generation to be reduced, while enhancing oxygen utilization and enabling milder operating conditions to be employed, the invention provides highly desirable technical, economic and environmental advantage over conventional TPA production operations.

We claim:

1. An improved process for the production of terephthalic acid comprising:
    (a) maintaining a portion of a body of liquid in a recirculating flow condition in a reactor vessel, said liquid containing p-xylene reactant, solvent, catalyst and a bromine initiator, the recirculating portion of the body of liquid having no gas-liquid interface with an overhead gas phase, said recirculating portion of the body of liquid being separated by mechanical means from, but in fluid communication with, a relatively quiescent portion of the body of liquid, said quiescent portion of the body of liquid having a gas-liquid interface with an overhead gas phase and being adapted to accommodate a change in liquid level in response to a change in the volume in the body of liquid between the condition in which essentially no gas bubbles are in the body of liquid and the condition that exists when a desired gas bubble concentration is developed within said body of liquid;
    (b) introducing a feed stream of essentially pure oxygen, or oxygen-enriched air containing at least about 50% oxygen, directly into the recirculating portion of said body of liquid, and not into said quiescent portion thereof, the recirculating flow path and flow velocity of said recirculating portion of the body of liquid being such, relative to the fluid communication between said recirculating and quiescent portions of the body of liquid, that the oxygen bubbles formed upon the introduction of the feed stream into the recirculating portion of the body of liquid are maintained in dispersed form in the recirculating liquid, for oxygen dissolution in, and reaction with, the p-xylene reactant in the recirculating portion of the body of liquid, without any appreciable passage of said oxygen bubbles through the fluid communication between the recirculating portion of the body of liquid and the quiescent portion thereof and through the quiescent portion thereof to the gas-liquid interface, and thus without loss of oxygen to the overhead gas phase;
    (c) maintaining the oxygen-liquid mixture in the reactor vessel at a temperature of from about 150° C. to about 200° C., and a pressure of between about 100 psig and 200 psig, for a residence time of from about 30 to about 90 minutes; and
    (d) recovering desired terephthalic acid product from the reactor vessel, whereby said terephthalic acid is produced with the production of undesired by-products being decreased, and with advantageously low gas handling requirements, and decreased environmental impact concerns.

2. The process of claim 1 in which said solvent comprises acetic acid.

3. The process of claim 2 in which the solvent:p-xylene reactant ratio is from about 1:1 to about 8:1 on a wt/volume basis.

4. The process of claim 1 in which said catalyst comprises a mixture of cobalt and manganese catalysts.

5. The process of claim 4 in which said catalyst comprises a mixture of cobalt and manganese acetate, with the catalyst loading being between 500 and 3,000 ppm based on the volume of the liquid reaction mixture.

6. The process of claim 5 in which the ratio of cobalt catalyst to manganese catalyst is from 0.1:1 to 10:1 on a weight basis.

7. The process of claim 6 in which said ratio of cobalt catalyst to manganese catalyst is about 3:1.

8. The process of claim 1 in which said initiator comprises hydrogen bromide.

9. The process of claim 1 in which said feed stream comprises essentially pure oxygen.

10. The process of claim 1 in which said feed stream comprises oxygen-enriched air containing at least about 50% oxygen.

11. The process of claim 1 in which said temperature is about 180° C. and said pressure is from about 130 psig to about 150 psig.

12. The process of claim 11 in which said feed stream comprises essentially pure oxygen.

13. The process of claim 1 and including passing an inert gas through the overhead gas phase in the reactor vessel to purge oxygen therefrom.

14. The process of claim 1 in which said recirculating portion of liquid is maintained in a recirculating flow condition by the essentially central positioning therein of a hollow draft chamber such that the open ends thereof are at the bottom and top thereof, impeller means being positioned within said hollow draft chamber to cause the oxygen-liquid mixture in the major portion of the body of liquid to pass through said hollow draft tube.

15. The process of claim 14 in which said recirculating portion of the body of liquid is separated from said quiescent portion thereof by baffle means positioned in said body of liquid, said positioning being such as to obviate the accumulation of individual oxygen bubbles thereunder.

16. An improved process for the production of terephthalic acid comprising:
   (a) maintaining a body of liquid in a recirculating flow condition in a reactor vessel by impeller means, said liquid containing p-xylene reactant, solvent, catalyst and a bromine initiator;
   (b) introducing a feed stream of essentially pure oxygen, or oxygen-enriched air containing at least about 50% oxygen, into said recirculating body of liquid for dispersion and dissolution in the body of liquid, and reaction with the p-xylene reactant;
   (c) maintaining the oxygen-liquid mixture in the reactor vessel at a temperature of from about 150° C. to about 200° C., and a pressure of between about 100 psig and 200 psig, for a residence time of from about 30 to about 90 minutes;
   (d) passing a sufficient quantity of inert gas through the overhead gas phase in the reactor vessel to purge oxygen therefrom; and
   (e) recovering desired terephthalic acid produced from the reactor vessel, whereby the terephthalic acid is produced with minimum production of undesired by-products, and will thereby reduced environmental impact concerns.

17. The process of claim 16 in which said solvent comprises acetic acid.

18. The process of claim 16 in which said catalyst comprises a mixture of cobalt acetate and manganese acetate in a ratio of from about 0.1:1 to 10:1 on a weight basis.

19. The process of claim 16 in which said feed stream comprises essentially pure oxygen.

20. The process of claim 16 in which said initiator comprises hydrogen bromide.

* * * * *